US007754940B2

(12) United States Patent
Brisebois et al.

(10) Patent No.: US 7,754,940 B2
(45) Date of Patent: Jul. 13, 2010

(54) THIN SANITARY NAPKIN HAVING PROTRUSIONS

(75) Inventors: Henri Brisebois, Lachenaie (CA); Louis Canuel, Repentigny (CA); Christiane Lariviere, Montreal (CA); Anthony Schoonen, Roxboro (CA)

(73) Assignee: Johnson & Johnson Inc., Montreal, Quebec (CA)

( * ) Notice: Subject to any disclaimer, the term of this patent is extended or adjusted under 35 U.S.C. 154(b) by 1017 days.

(21) Appl. No.: 10/460,003

(22) Filed: Jun. 12, 2003

(65) Prior Publication Data

US 2004/0254556 A1    Dec. 16, 2004

(51) Int. Cl.
*A61F 13/15* (2006.01)
*A61F 13/20* (2006.01)

(52) U.S. Cl. .............. 604/380; 604/378; 604/379; 604/385.101

(58) Field of Classification Search ............ 604/385.01, 604/378, 380
See application file for complete search history.

(56) References Cited

U.S. PATENT DOCUMENTS

| 3,236,238 A | 2/1966 | Morse |
| 4,315,507 A | 2/1982 | Whitehead et al. |
| 5,728,446 A * | 3/1998 | Johnston et al. ............. 428/167 |
| 5,993,431 A | 11/1999 | McFall et al. |
| 6,171,682 B1 | 1/2001 | Raidel et al. |
| 6,425,890 B1 | 7/2002 | Samuelsson et al. |
| 6,432,094 B1 | 8/2002 | Fujioka et al. |
| 6,500,159 B1 | 12/2002 | Carvalho |
| 6,525,239 B2 * | 2/2003 | Cole ............................ 604/382 |
| 2002/0062114 A1 * | 5/2002 | Murai et al. ............ 604/385.01 |
| 2002/0065498 A1 * | 5/2002 | Ohashi et al. ................ 604/379 |
| 2002/0143309 A1 * | 10/2002 | Glasgow et al. ........ 604/385.01 |
| 2002/0174934 A1 | 11/2002 | Johnson et al. |
| 2003/0093047 A1 * | 5/2003 | Nguyen et al. ............... 604/368 |
| 2004/0236294 A1 * | 11/2004 | Drzewiecki et al. .......... 604/366 |

FOREIGN PATENT DOCUMENTS

| CN | 1430942 A | 7/2003 |
| EP | 1022007 B1 | 7/2000 |
| EP | 1138300 | 10/2001 |
| EP | 1190690 A2 * | 3/2002 |
| WO | 94/16658 A1 | 8/1994 |

* cited by examiner

*Primary Examiner*—Melanie J Hand (57) ABSTRACT

A sanitary absorbent article is disclosed which is intended to be worn against a pudendal region of a user. The sanitary absorbent article is thin, i.e. having a thickness equal to or less than 5 mm and comprises a body contacting surface with at least one protrusion on the body contacting surface. The protrusion has a height H of at least 0.5 mm, and an equivalent width W. The protrusion also includes a ratio W/H ranging from about 2 to about 10.

26 Claims, 7 Drawing Sheets

THIN SANITARY NAPKIN HAVING PROTRUSIONS

CROSS-REFERENCE TO RELATED APPLICATIONS

1. Field of the Invention

The present invention relates to disposable sanitary absorbent articles and, in particular, to a thin sanitary napkin having one or more protrusions on its body-contacting surface.

2. Background of the Invention

In recent years, an ever-increasing trend among users of sanitary napkins has been to use napkins which are less voluminous or bulky, and thus less restricting and less apt to show. This is especially the case since tight-fitting garments are more and more in vogue among contemporary women.

However, due to their size, thin sanitary napkins are often limited in their fluid management properties, and particularly in their ability to rapidly absorb liquid discharges. Furthermore, thin sanitary napkins often do not convey to a prospective user that they are able to absorb and retain bodily exudates. As such, a user often has less confidence in a thinner sanitary napkin than a thicker sanitary napkin. A balance between a sanitary napkin's functionality and appearance must therefore be achieved by manufacturers of sanitary napkins. The term "sanitary napkin", as used herein, refers to sanitary absorbent articles that are worn by females in their undergarments adjacent to the pudendal region, and which are intended to absorb and contain the various exudates that are discharged from the body (e.g., blood, menses, vaginal discharges and urine). Hence, the term "sanitary napkin" encompasses pantiliners in addition to catamenial devices. The term "disposable" refers to articles that are intended to be discarded after a single use and preferably recycled, composted, or otherwise disposed of in an environmentally friendly manner.

Considering this background, it clearly appears that there is a need in the industry to develop a feminine sanitary napkin that is thin, and yet has good fluid management properties and a visual appearance that conveys to an end user a feeling of reassurance in terms of its functionality.

SUMMARY OF THE INVENTION

In accordance with the present invention there has been provided a sanitary absorbent article which is intended to be worn against a pudendal region of a user. The sanitary absorbent article is generally thin, i.e. it has a thickness equal to or less than 5 mm and comprises a body-contacting surface having at least one protrusion. The protrusion has a height H and an equivalent width W, wherein the height H is at least 0.5 mm and the ratio of width to height the sanitary napkin with a low fluid penetration time.

BRIEF DESCRIPTION OF THE DRAWINGS

A detailed description of preferred embodiments of the present invention is provided herein below with reference to the following drawings, in which:

FIG. 3b is an enlarged fragmentary view of a portion of FIG. 3a;

FIG. 4b is an enlarged fragmentary view of a portion of FIG. 4a;

FIG. 7b is an enlarged fragmentary view of a portion of FIG. 6a.

In the drawings, preferred embodiments of the invention are illustrated by way of examples. It is to be expressly understood that the description and the drawings are only for the purpose of illustration and as an aid to understanding. They are not intended to be a definition of the limits of the invention.

DETAILED DESCRIPTION

Figure 1:
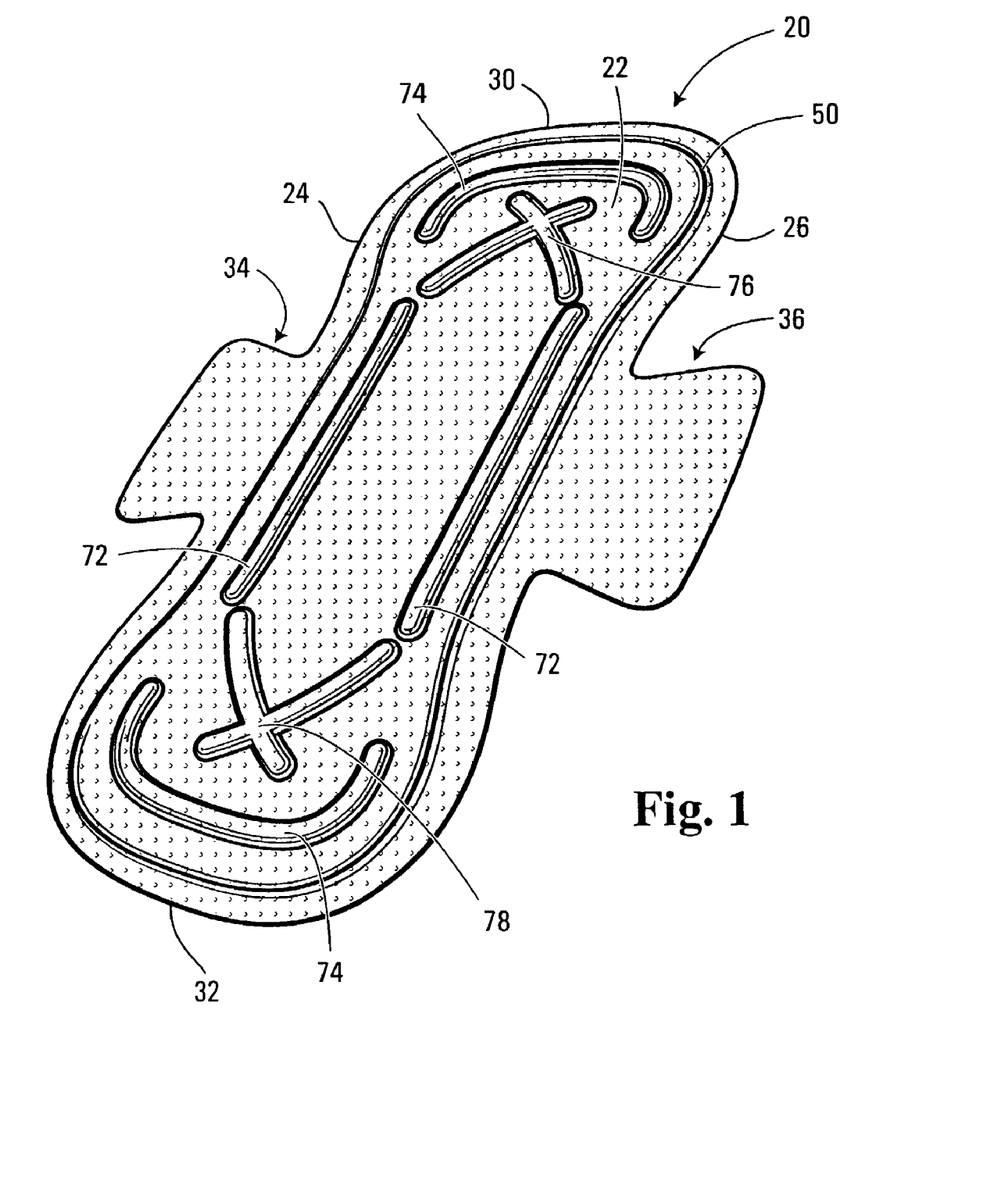
FIG. 1 is a perspective view of a first non-limiting example of a sanitary napkin of the present invention.
Figure 2:
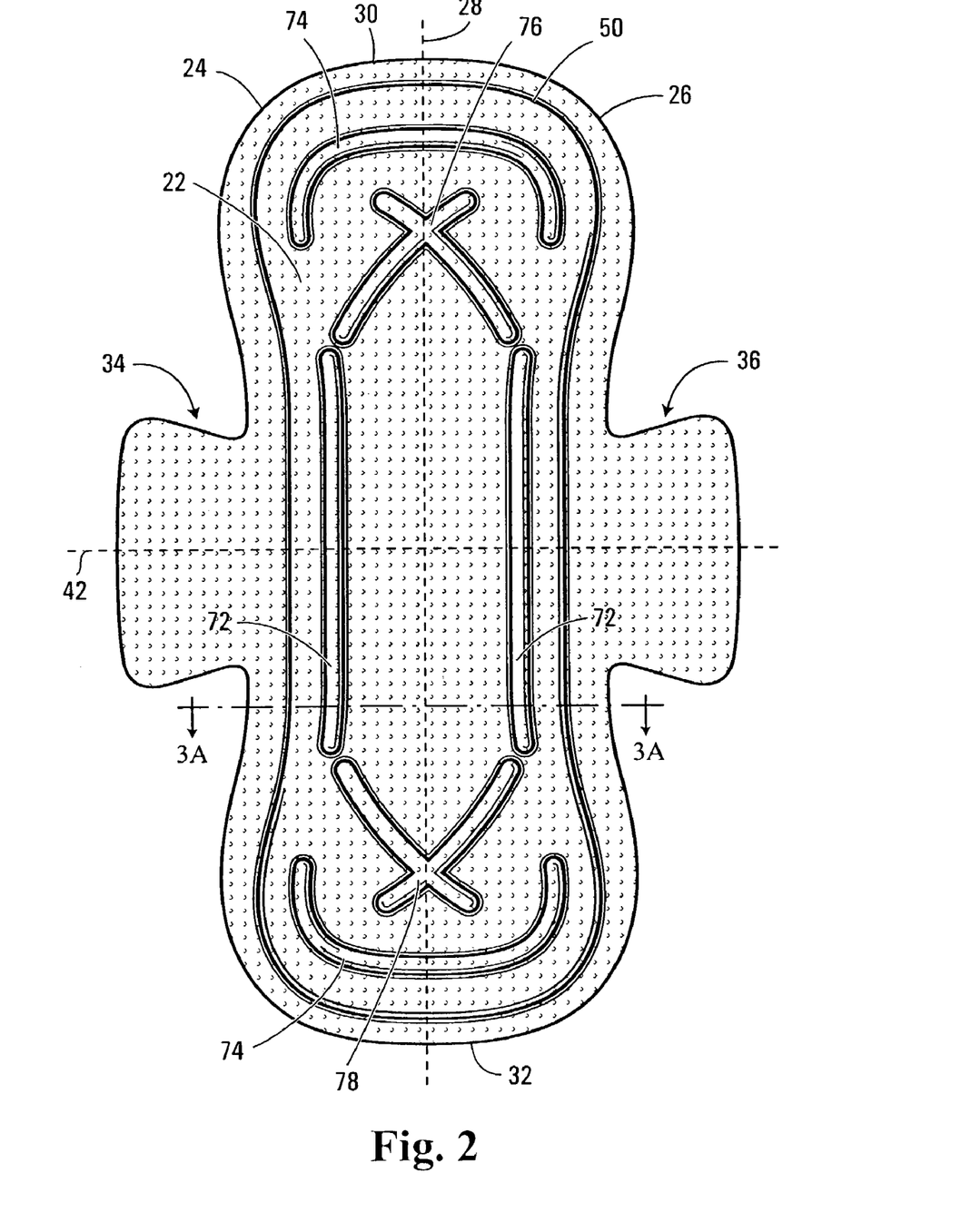
FIG. 2 is a top plan view of the sanitary napkin of FIG. 1.

FIGS. 1 to 2 show a non-limiting example of a sanitary absorbent article such as, for example, a sanitary napkin 20. The sanitary napkin 20 comprises a main body 22 having generally opposing longitudinal side edges 24, 26, and an imaginary longitudinal centerline 28 running down the center of the sanitary napkin, generally equidistant from the longitudinal side edges 24, 26. In addition, the main body 22 also has two generally opposing transverse sides 30, 32, and an imaginary transversal centerline 42 that runs across the body of absorbent article 20, thereby intersecting the imaginary longitudinal centerline 28. The term "longitudinal", as used herein, refers to a line, axis or direction in the plane of the absorbent article 20 that is generally aligned with (e.g., approximately parallel to) a vertical plane which bisects a standing wearer into left and right body halves when the absorbent article 20 is worn. sanitary napkin 20 includes a plurality of protrusions 72, 74, 76 and 78 on its body contacting surface (i.e., on cover layer 56). The protrusions 72, 74, 76 and 78 extend above a reference plane R (as shown in FIG. 3a) which lies on the planar portion of the body contacting surface of the fluid pervious cover layer 56.

Flaps 34, 36 respectively project laterally from each of the longitudinal side edges 24, 26 away from the longitudinal centerline 28 of the main body 22. It should be noted, however, that sanitary napkins having no flaps also remain within the scope of the present invention.

Figure 3A:
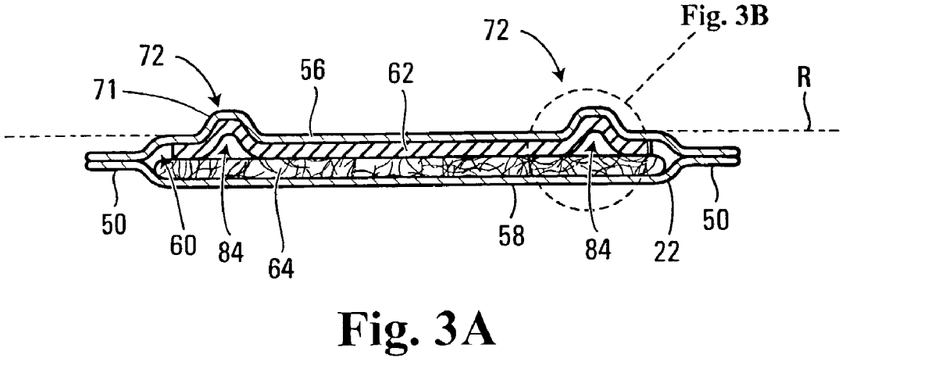
FIG. 3a is a cross-sectional view taken along line 3a-3a of FIG. 2.

FIG. 3a shows a cross section of a sanitary napkin 20, featuring a laminate structure with main body 22 generally including: a fluid-permeable cover layer 56, having a body-contacting surface when the napkin is in use; a liquid-impervious barrier layer 58, having a garment facing surface when the napkin is in use; and an absorbent system 60 therebetween. The absorbent system 60 may have a single layer or, alternatively, a plurality of layers. In the example of implementation depicted in the drawings, absorbent system 60 includes a multi-layer structure. Specifically, the absorbent system 60 has a first layer, called "transfer layer" 62, immediately underneath the fluid-permeable cover layer 56, and a second layer, called "absorbent core layer" 64, between transfer layer 62 and liquid-impervious barrier layer 58. The fluid-permeable cover layer 56 and the liquid-impervious barrier layer 58 are sealed together along their peripheral edges (including the flaps 34, 36) to form a peripheral seal 50 (shown in FIG. 2), containing the absorbent system 60. Peripheral seal 50 can be realized by using any means commonly known in the art such as by gluing, crimping, pressure and/or heat sealing, ultrasonics, and the like. In addition, although peripheral seal 50 is shown as being continuous, the present invention also contemplates embodiments where the peripheral seal 50 is intermittent and does not therefore fully enclose absorbent system 60. Thus, a variety of seal configurations are within the scope of the present invention.

Each of the layers mentioned above will now be described in greater detail.

Fluid-Permeable Cover Layer

With reference to FIGS. 1 to 3b, the fluid-permeable cover layer 56 is the top layer of the sanitary napkin 20. The purpose of the fluid-permeable cover layer 56 is to provide an interface that would normally contact the body of the wearer when the sanitary napkin 20 is in use. The fluid-permeable cover layer 56 is porous to liquids since its main function is to capture as quickly as possible a discharge of bodily exudate and transfer it to the absorbent system 60 underneath.

Under one specific example of implementation, the fluid-permeable cover layer 56 is formed from an apertured thermoplastic film. Such films are common in the art. Because of the high porosity of such films, they accomplish the function of quickly transferring body exudate to the inner layers (i.e. the absorbent system 60) of the napkin 20.

The fluid-permeable cover layer 56 can also be made of fibrous materials, such as non-woven fibrous materials. The fluid-permeable cover layer 56 may be composed of only one type of fiber, such as polyester, or may be composed of bicomponent or conjugate fibers having a low melting point component and a high melting point component. Bicomponent fibers may be made up of a polyester core and a polyethylene sheath. The use of appropriate bicomponent materials results in a fusible non-woven fabric. Using a fusible fabric increases the ease with which the fluid-permeable cover layer 56 may be mounted to the barrier layer 58 at the peripheral seal 50.

The fibers may be selected from a variety of natural and synthetic materials such as nylon, polyester, rayon (in combination with other fibers), cotton acrylic fiber and the like, and combinations thereof. It will be evident to the person skilled in the art that a wide variety of other types of non-woven fabric materials can also be used.

Transfer Layer

Subjacent to the fluid-permeable cover layer 56 on its inner side and preferably bonded thereto is the fluid transfer layer 62, that may form part of the absorbent system 60. The transfer layer 62 provides a means of rapidly receiving body fluid from the fluid-permeable cover layer 56 and holding it until the highly-dense, slower absorbing absorbent core layer 64 has an opportunity to absorb it.

The transfer layer 62 is, preferably, more dense than the fluid-permeable cover layer 56 and has a larger proportion of smaller pores than does the latter. These attributes allow the transfer layer 62 to contain body fluid and hold it away from the outer side of the fluid-permeable cover layer 56, thereby preventing the fluid from re-wetting the fluid-permeable cover layer 56 and its surface.

The transfer layer 62 may be composed of fibrous materials such as wood pulp, polyester, rayon, flexible foam, or the like, or combinations thereof. The transfer layer 62 may also comprise thermoplastic fibers for the purpose of stabilizing the layer and maintaining its structural integrity. The transfer layer 62 may be treated with surfactant on one or both of its sides in order to increase its wettability. However, the transfer layer 62 is generally relatively hydrophilic and may not require additional treatment. The transfer layer 62 is preferably bonded on both sides to the adjacent layers, i.e. the fluid-permeable cover layer 56 and the absorbent core layer 64.

Absorbent Core Layer

Immediately subjacent to and bonded to the transfer layer 62 is the absorbent core layer 64; the latter also forming part of the absorbent system 60. The absorbent system 60 may comprise only the absorbent core layer 64 or it may comprise a plurality of layers, such as the absorbent core layer 64 in combination with the transfer layer 62 or any other additional layer.

The absorbent core layer 64 is a highly dense layer having a fine porosity. It has a large liquid-holding capacity and it is extremely retentive. Preferably, the absorbent layer 64 comprises a pulp fluff material and may optionally include other absorbent materials or non-absorbent materials such as conjugate fibers, fusible fibers, binders, sphagnum moss, super-absorbents, and the like and combinations thereof.

Liquid-Impervious Barrier Layer

Underlying the absorbent system 60 is a liquid-impervious barrier layer 58. The liquid impervious barrier layer comprises liquid-impervious film material such as to prevent liquid that is entrapped in the absorbent core layer 64 from egressing the sanitary napkin 20 and staining the wearer's undergarment. The liquid-impervious barrier layer 58 can be made of polymeric film, such as polyethylene or a polyethylene/ethylvinyl acetate (EVA), which are both inexpensive and readily available. The polymeric film is capable of fully blocking the passage of liquid or gas that may emanate from the absorbent system 60. In a variant, breathable films may be used that allow passage of gases while blocking liquid.

Thickness of the Sanitary Napkin

The sanitary napkin 20 has a thickness T of about 5 mm or less in the dry state. The term "thickness" as used herein, refers to caliper of the product and, for purposes of this invention is defined as the distance between the garment facing surface of the liquid-impervious barrier layer 58 and the highest point on the body-contacting surface of the fluid permeable cover layer 56 (thickness T shown in FIG. 3B). One apparatus that has been found to be suitable for measuring the thickness of the sanitary napkin 20 is a footed dial (thickness) gauge, available from Ames B.C. Co. of Melrose, Mass., with foot 1⅛" diameter with stand, 2 oz. deadweight accurate to 0.001". A digital type apparatus is preferred.

If the sanitary napkin is individually folded and wrapped, the sample is unwrapped and carefully flattened by hand. The release paper is removed from the sample and it is repositioned back gently across the positioning adhesive lines so as to not compress the sample. Flaps (if any) are folded back under the sample, prior to taking the thickness reading in the center of the sample.

The foot of the gauge is raised and the sample is placed on the anvil such that the foot of the gauge is approximately centered to the sample (or in the location of interest on the sample of interest). When lowering the foot, care is taken to avoid allowing the foot to "drop" or that undue force is not applied. The read out is allowed to stabilize for approximately 5 seconds, and the thickness reading is then taken.

Protrusions

Referring again to FIGS. 1 to 4b, sanitary napkin 20 includes a plurality of protrusions 72 which respectively extend along longitudinal side edges 24, 26 (and thus along imaginary longitudinal centerline 28 and a pair of protrusions 74 which respectively extend along transverse sides 30, 32 (and thus along imaginary transverse centerline 42), 76 and 78 on its body contacting surface (i.e., on cover layer 56). The sanitary napkin 20 also features a pair of protrusions 76, 78 in a more central area of main body 22, meaning that they extend towards the longitudinal centerline of the main body 22. Protrusions 76, 78 intersect one another such that they share a common boundary. In addition, protrusions 76 and 78 run obliquely with respect to the imaginary longitudinal centerline 28. The protrusions 72, 74, 76 and 78 extend above a reference plane R (as shown in FIG. 3a) which lies on the planar portion of the body contacting surface of the fluid pervious cover layer 56. FIGS. 1 and 2 show protrusions 72, 74, 76 and 78 having an elongated and generally rectangular shape, however, it should be specifically understood that protrusions having different shapes remain within the scope of the present invention. For example, the protrusions could be in the shape of a square or a parallelogram (i.e., such as a diamond shaped lozenge). Moreover, the protrusions could be of circular or elliptic shape.

FIGS. 1 and 2 also show that protrusions 72, 74, 76 and 78 define a protrusion pattern which is symmetrical about both the imaginary longitudinal centerline 28 and the imaginary transverse centerline 42. However, it should be noted that the protrusions could also define a protrusion pattern which is symmetrical along a single one of the imaginary longitudinal centerline 28 or the imaginary transverse centerline 42. Alternatively, the protrusions can be randomly distributed along the sanitary napkin's 20 body contacting surface such as to define a protrusion pattern which is not symmetrical along either one or both the imaginary centerlines. Protrusions 72, 74, and 76 are spaced from one another on the surface of the main body 22 such that they are not in contact with each other.

Figure 3B:
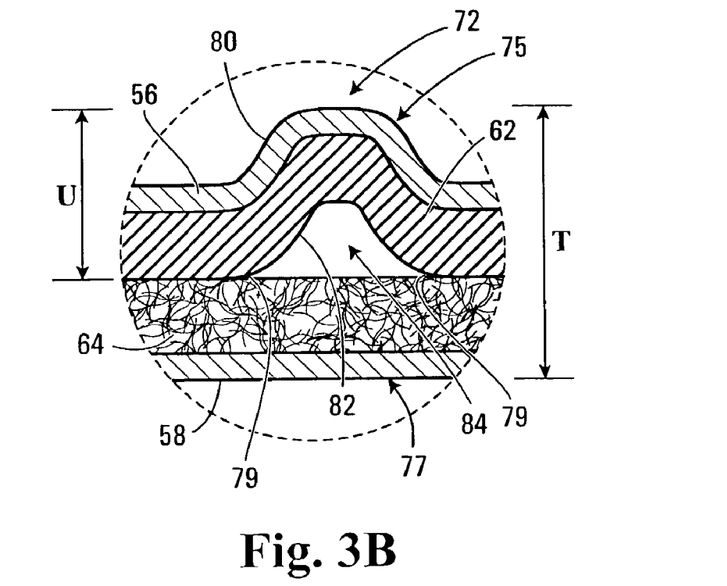

As shown in FIGS. 3a and 3b, the protrusions are formed as an integral part of at least one layer of the sanitary napkin 20, meaning that they are formed out of the material of at least one of the layers of the sanitary napkin 20, and are not distinct parts that are affixed to the main body 22. Shown in FIG. 3b, is an upper treated component 75 that includes protrusions 72 that are formed of the fluid-pervious cover layer 56 and the transfer layer 62, which are positioned immediately adjacent one another, meaning that they lie on top of one another. In an alternative example of implementation shown in FIGS. 4a and 4b, the upper treated component 75 includes protrusions 72 that are formed of the fluid-permeable cover layer 56, the transfer layer 62, and the absorbent core layer 64. It should be specifically understood, however, that any of the layers of the sanitary napkin 20 (including the liquid-impervious barrier layer 58 depicted in FIGS. 3a and 3b) can be treated so as to form the upper treated component 75 having projections, irrespective of what is shown in FIGS. 3a, 3b, 4a and 4b.

FIGS. 3a, 3b, 4a and 4b further show that the upper treated component 75 has a pair of main surfaces 80, 82 which are opposite one another. The treated component 75 includes protrusions 72 on main surface 80 and recesses 84 on main surface 82. Note that, in this case, each recess 84 registers with its corresponding protrusion 72 due to the method of manufacture, which will be described in more detail further on with respect to FIGS. 7a and 7b. Each recess 84 is delimited by the upper treated component 75 as well as a lower component 77 (shown in FIGS. 3B and 4B). As such, the spacing between the treated component 75 and the lower component 77 is greater within the boundary 79 of a recess 84 than outside the boundary 79 of a recess 84. In the case of FIGS. 3a and 3b, the lower component 77 includes the absorbent core layer 64 and the barrier layer 58 and in the case of FIGS. 4a and 4b, the lower component 77 includes only the barrier layer 58. It should be noted, however, that absorbent core layer 64 could also be part of the treated component 75, as mentioned previously. When considering FIGS. 1 to 4b, it should be apparent to the reader that the recesses 84 form some type of inner cavity within sanitary napkin 22. In this specific case, the recesses 84 form an inner channel.

Moreover, although FIGS. 3a, 3b, 4a and 4b show the lower component 77 as being substantially planar when the sanitary napkin 20 is laid flat, it should be understood that a lower component 77 having a shape which is not planar also remains within the scope of the present invention. In addition, the recesses 84 shown in the figures are essentially void areas (or in the very least low-density areas), meaning that essentially no other material is present therein. However, in a variant not shown, each recess 84 could also contain additional material therein which is different than that which forms the upper treated component 75 and the lower component 77. For example, the recesses 84 could include a filler material, such as super absorbent polymer (SAP), odor control materials, or other functional materials in particulate or solid form.

Figure 4A:
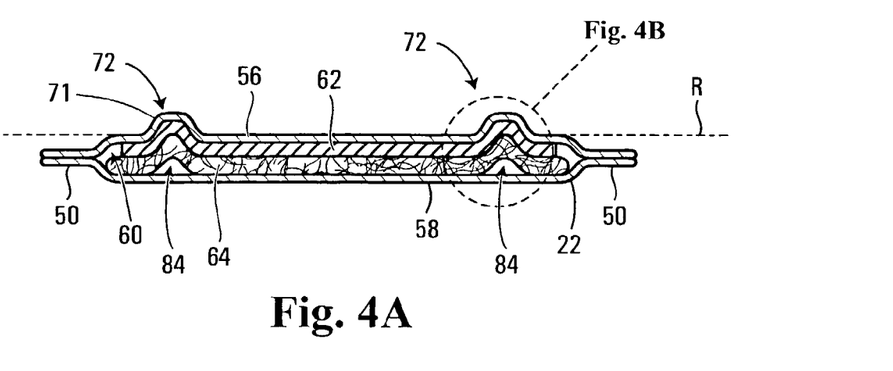
FIG. 4a is a cross-sectional view of a sanitary napkin in accordance with an alternative embodiment of the present invention.
Figure 4B:
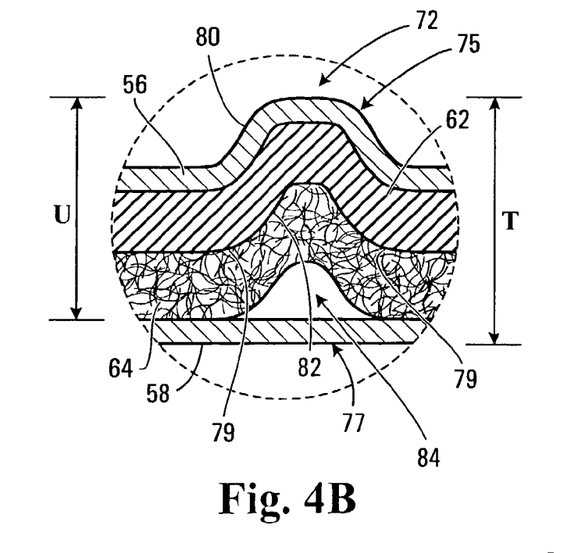

FIGS. 3b and 4b also show that the upper treated component 75 is characterized by a thickness U which is fairly substantial when compared with the total thickness T of sanitary napkin 20. For example, the sanitary napkin 20 may have a ratio U/T of at least 0.2.

Each of the protrusions 72, 74, 76, and 78 on the main body 22 of the sanitary napkin extends by a height H of at least 0.5 mm above the reference plane R, and has a width to height W/H ratio which generally varies between about 2 and about 10.

The inventors have found that sanitary napkins 20 having protrusions with a height H and a width to height ratio W/H as described in the present application, advantageously convey to a user the appearance of thickness, which instills in the user a sense of confidence that the sanitary napkin will be able to absorb and retain bodily exudates. In addition, the inventors have found that sanitary napkins 20 having protrusions as described herein have a lower penetration time. "Penetration time" is defined as the time taken for the sanitary napkin 20 to absorb a predetermined quantity of a specific liquid.

Without wishing to be bound by a specific theory or mechanism of action, the sanitary napkin 20 of the present invention is believed to demonstrate low penetration times due to the fact that the protrusions provide an increased surface area over which the fluid can be absorbed, and that the fluid impinging upon the protrusions may be partially directed downward into the absorbent structure and partially directed from the protrusions into the recesses 84. This allows fluid, even relatively viscous fluid and fluid with high solids content to penetrate the sanitary napkin 20 and be rapidly directed away from the wearer.

The methods for measuring the height H and equivalent width W will now be described with reference to FIGS. 4 to 5B.

Height

Figure 5:
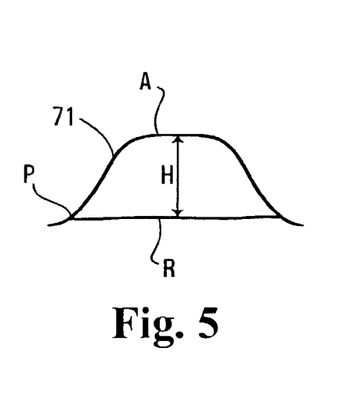
FIG. 5 is a schematic cross-sectional view of a protrusion.

As shown in FIG. 5, the height H corresponds to the vertical distance between the imaginary reference plane R and the most elevated portion, or apex A, of a given protrusion. The height H of the protrusions extends by at least 0.5 mm above the reference plane R. It is therefore implicitly understood that protrusions having a height H that extends above 0.5 mm remain within the spirit of the invention. For example, the protrusions could have a height H that extends up to 2.0 mm above the reference plane R. Moreover, the protrusions 72, 74, 76, and 78 also have a ratio W/H ranging between about 2 and about 10. However, the ratio W/H could more restrictively range between 3 to 9, between 4 to 8, or between 5 to 7.

The imaginary reference plane R is established by the following procedure. Firstly, a point of origin P is identified on the given protrusion. A point of origin P is a point of inflection at which a sidewall 71 of the protrusion joins the layer containing the protrusion (e.g., the cover layer 56). An isolated protrusion is likely to have an infinite number of points of origin P that form a continuous line circumscribing the protrusion.

Figure 9A:
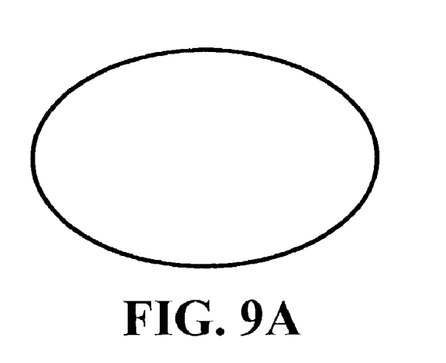
FIGS. 9A and 9B show examples of a simply connected space and a multiply connected space.
Figure 9B:
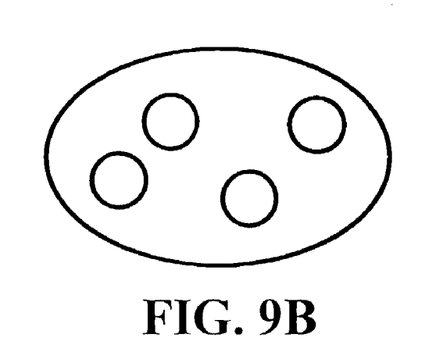

The imaginary reference plane R contains the point of origin P, as defined earlier. The plane R must intersect the sidewalls 71 of the protrusion, thereby defining a connected bi-dimensional space. The bi-dimensional space can be a simply connected space (as shown in FIG. 9A), or a multiply connected space (as shown in FIG. 9B). A space is simply connected if every loop made within that space is contractible to a single point. In other words, a simply connected space has no "holes". If all the points of origin P are at the same vertical elevation, the imaginary reference plane R will intersect the protrusion's side walls at all of its points of origin. In such a case, the points of origin will collectively define the boundary of the protrusion. Protrusions may exist in which the reference plane will not intersect all of the points of origin P. This occurs when at least some of the points of origin are at a different vertical elevation than others. Any reference plane including a point of origin P, that intersects the protrusion to form either a simply connected space or a multiply connected space will define a boundary of the protrusion. It should be noted that a number of different imaginary reference planes could be defined for a given protrusion depending on the choice of the point of origin.

It should also be expressly understood that each protrusion may have more than one apex. For example, if the protrusion is in the form of a level raised area (as in FIG. 5), then there would be a plurality of apexes which would define a plateau. Moreover, if the protrusion is in the form of a series of steps, then there would be a plurality of apexes defining the most elevated step or plateau. If, however, the protrusion is in the form of a single triangle, then there would be a single apex.

Procedure for Determining Height and Width of Protrusions

Once the imaginary reference plane R is established and the apex A is identified for a given protrusion, then the height H and width W can be measured. These measurements can be done by using any appropriate method such as, for example, using a microscope capable of determining focal distances. Examples of such microscopes are commercialized by Edmund Scientific, among others.

An alternative would be to use a more refined automated method. For accurate measurements of the height and width of the protrusions 72, 74, 76, and 78 it is preferred that an optical measurement system be employed. For example, one particular method that is capable of accurately determining the height and width of the protrusions 72, 74, 76, and 78 involves the use of a digital stripe protrusion technique, which can be performed using a system such as the PRIMOS optical 3D skin measurement system, commercially available from GFMesstechnik GmbH of Berlin, Germany. Although the PRIMOS optical 3D skin measurement system is generally used for taking in vivo skin measurements, it can also be used to take 3D surface measurements of inanimate objects, such as sanitary napkins.

Figure 8:
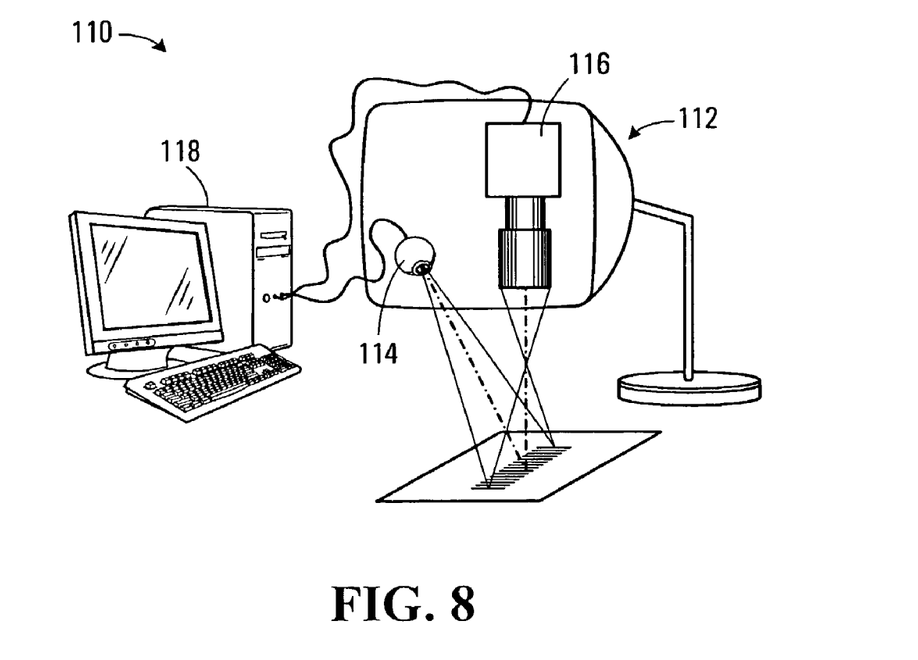
FIG. 8 shows a schematic diagram of a measurement system for taking height and width measurements in accordance with a specific example of implementation.

Shown in FIG. 8, is a schematic representation of an optical 3D measurement system 110 that is suitable for obtaining 3D surface measurements of the fluid management article, such as the sanitary napkin 20 of the present invention. The optical 3D measurement system 110 includes an optical measurement head 112 having a light projector 114, a CCD recording camera 116 and a protrusion and shooting optic (not shown). The light projector 114 may be a digital micromirror projector such as a Digital Micromirror Device (DMD) that is available from Texas Instruments of Houston, Tex. In operation, the light projector 116 projects a series of alternating black and white parallel stripe patterns onto the surface of the sanitary napkin, wherein each stripe pattern has stripes of different widths. The minute elevation differences on the surface of the sanitary napkin 20 distort the parallel stripes, and it is these distortions that constitute a qualitative and quantitative representation of the surface profile of the sanitary napkin 20.

The CCD recording camera 116 acquires the pictures of the distorted stripe patterns and forwards them to a processing unit 118, such as a personal computer, that is connected to the optical measurement head 112. The processing unit 118 is operative to drive the light projector 114 and receive signals from the CCD recording camera 116. The pictures acquired by the CCD recording camera 116 and received by the processing unit 118 are analyzed by the processing unit 118 in order to derive surface measurements of the sanitary napkins being measured. The processing unit 118 may employ PRIMUS SOFT software, also commercially available from GFMesstechnik of Berlin, Germany, in order to interpret the data from the CCD recording camera 116.

One suitable process for obtaining height measurements using the PRIMOS optical 3D measurement system 110, is as follows. Firstly, the optical 3D measurement system 110, including the light projector 114, a CCD recording camera 116, and the processing unit 118 are powered and allowed to warm up. Once warmed up, the "technical surface" setting is selected, which is the appropriate setting for obtaining surface measurements of inanimate objects. The next step is to perform a calibration procedure. For example, in order to calibrate the PRIMOS optical 3D measurement system 110, a calibration block having a trench of a certain vertical depth is placed under the optical measurement head 112 and the focus and light intensity of the equipment are adjusted. In order to adjust the light intensity, a light adjustment knob located on the camera is manually adjusted until a visual indicator in the form of a circle that changes color, turns green. The green circle indicates that the light intensity is properly set. The focus is adjusted by adjusting a red-screen cross hair such that it is in alignment with a black cross hair.

Once the light intensity and focus have been set, the user hits the "measure" button. The "measure" button causes the PRIMUS SOFT program to generate an index color image of the reference blocks surface, which is shown to a user on a display screen. The index color image shows the object's surface in different colors depending on the surface's different vertical heights. A profile line is drawn perpendicular to the reference block's trench on the display screen using a mouse or other suitable user interface. The PRIMUS SOFT software then generates a two dimensional graph of the reference block's surface profile along that profile line. In order to determine the height of the trench, the mouse is then clicked on the two dimensional graph at a location that represents the top surface of the reference block. The mouse is then clicked a second time on the two dimensional graph at a location that appears to be the bottom of the trench. The user then selects a vertical distance function from a tool bar or from a drop down menu. The vertical distance function provides the vertical distance between the two locations on the profile where the mouse was clicked. That vertical distance is then compared to the reference distance indicated on the reference block. If the measured distance is within 1% of the distance indicated on the reference block, then the PRIMUS optical 3D measurement system 110 is calibrated.

Once calibrated, the reference block is removed, and the sanitary napkin 20 is placed under the optical measurement head 112. The light intensity and focus are adjusted once more and the "measure" button is selected. The PRIMUS SOFT program generates an index color image of the sample being measured. A profile line is then drawn on the index color image perpendicular to the region where the height measurement is going to be taken.

A two dimensional graph of the sample's surface profile along that profile line is then generated. Once generated, the mouse is clicked on the two dimensional profile at a location that most closely approximates an imaginary reference plane R. The mouse is then clicked a second time at a location on the two dimensional graph that most closely approximates the apex A of a protrusion. The user then selects the vertical distance function, which provides the vertical distance between the two locations on the profile where the mouse was clicked, which in the case of the present invention would be the height of the protrusion.

In order to determine the width of a protrusion, the profile line is drawn across the width of the protrusion. A 2D profile of the sample's surface along that profile line is generated. The mouse is then clicked at the beginning and end of the section of the surface whose width is desired, and then the user selects a horizontal distance function from a toolbar or drop down menu. The horizontal distance function provides the distance between the two locations selected by the mouse, which in the case of the present invention could be the width of the protrusion.

To facilitate obtaining accurate measurements of the height and width, the optical measurement head 112 may use, for example, a 32 mm×32 mm field of view, with an x-y spatial resolution of 32 microns and a z-step resolution of 1 micron in order to obtain surface measurements of the sanitary napkin of the present invention. In addition, the point cloud from each acquisition may, for example, have 1,048,576 points (1024×1024).

It should be understood that a protrusion is considered to fall within the scope of the present invention as long as any one of the reference planes defines a protrusion with at least one apex, such that the protrusion satisfies the height H and equivalent W requirements, W being measured as defined below.

Width

Figure 6A:
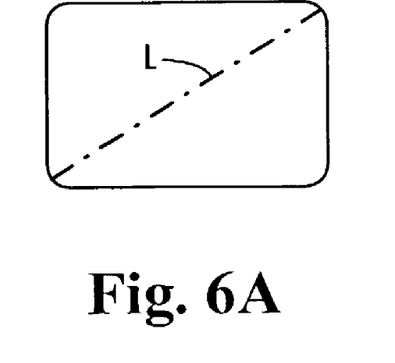
FIG. 6A is a schematic top plan view of a protrusion having a conventional shape.
Figure 6B:
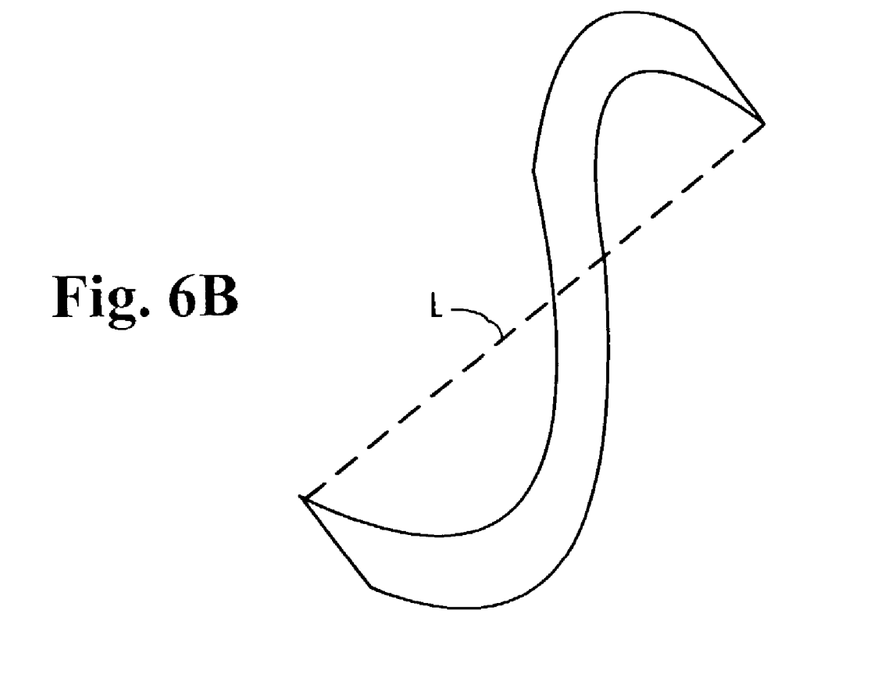
FIG. 6B is a schematic top plan view of a protrusion having a complex shape.

The equivalent width W of the protrusion is determined in the following manner. Firstly, a projected area of the closed 2-D figure, which was delimited during the calculation of the height of the protrusion, is computed. Then, the longest dimension L of the closed 2-D figure must be determined. FIG. 6A shows an example of how the longest dimension L is determined for a conventional shape while FIG. 6B shows an example of how the longest dimension L is determined for a complex shape. Finally, the equivalent width W of an imaginary figure (i.e., rectangle) having a surface area which is equivalent to the closed 2-D figure, and having a length L corresponding to the longest dimension L determined previously is computed.

One non-limiting method of computing the projected area of a complex shape, is using a planimetry method. In order to use a planimetry method in combination with the PRIMUS optical 3D measurement system 110 as described above, a reference block having a shape of known area is placed under the optical measurement head 112 and measured such that the PRIMUS SOFT program generates an index color image of that shape. A screen capture of the index color image is taken and is imported into a program such as PHOTOSHOP, which has an edge detection feature. Using the edge detection feature, the edges of the shape of known area are detected and the number of pixels contained within the boundaries of those detected edges is calculated. The known area is then divided by the number of pixels contained within the boundaries of that complex shape in order to determine the area covered by each pixel. Once this is complete, the reference block is removed and the sample containing the complex shape is placed under the optical measurement head 112 of the PRIMUS optical 3D measurement system 10 such that the PRIMUS SOFT program can generate an index color image of the complex shape. A screen capture of that index color image is taken and is imported into PHOTOSHOP in the same way as the screen capture of the reference block, as described above. The edge detection feature is then used to detect the edges of the complex shape, and the number of pixels contained within the boundaries of those detected edges is calculated. The number of pixels contained within the boundaries of the complex shape is then multiplied by the area covered by each pixel, as determined from the measurement of the shape on the reference block. This will provide a measurement of the projected area of the complex shape.

Method of Manufacture

Figure 7A:
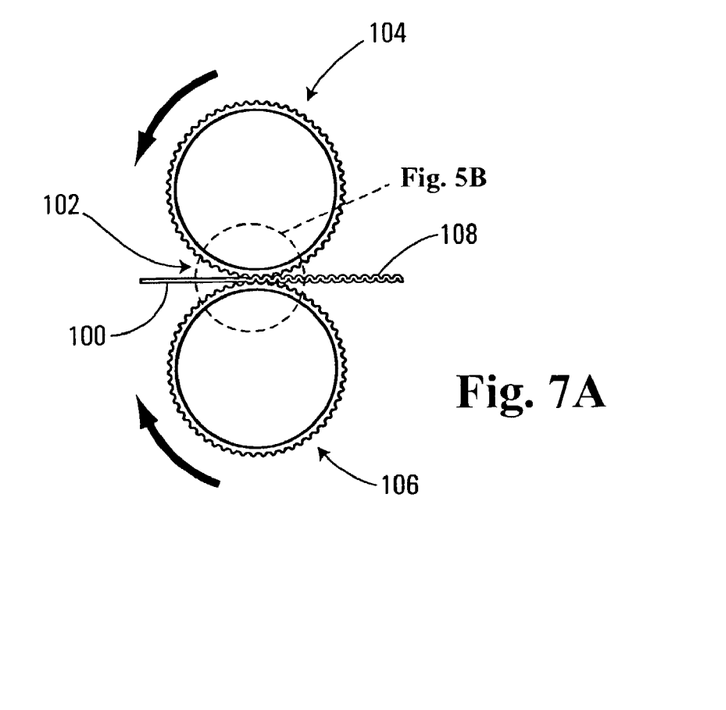
FIG. 7a is a schematic side view of an apparatus for forming a component of the sanitary napkin of FIG. 1.
Figure 7B:
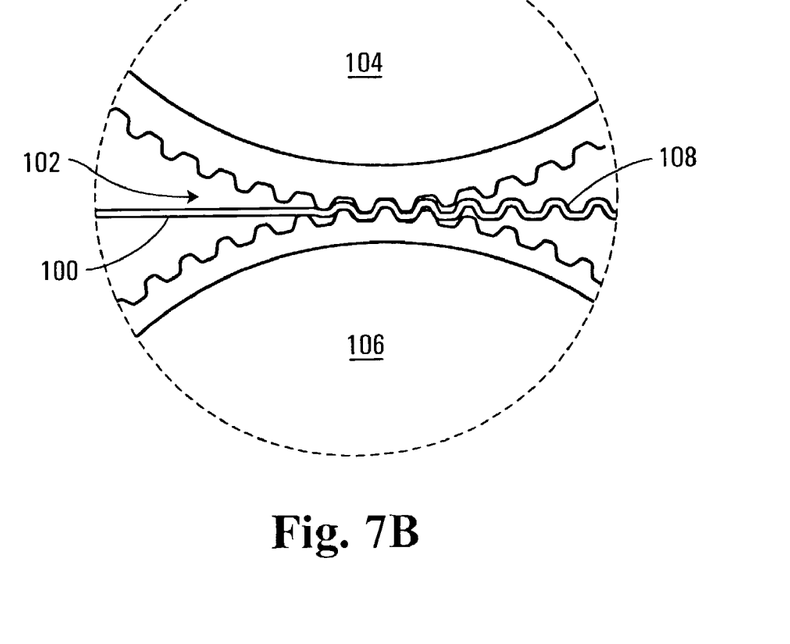

Sanitary napkins having protrusions can be manufactured using different methods. FIGS. 7a and 7b, for example, schematically depict one such method. More specifically, the figures show that a web of starting material 100, which will later form part of sanitary napkin 20, is fed through a nip 102 defined by a pair of patterned rolls 104, 106. As opposed to traditional embossing rolls, patterned rolls 104, 106 each respectively include teeth along their outer circumferences, which are adapted to intermesh with one another in a male-female relationship. Patterned rolls 104, 106 thereby form a profiled component 108 (i.e., with protrusions) from the web of starting material 100. This profiled component 108 can then be used in a subsequent step (not shown) to form sanitary napkin 20.

FIGS. 7a and 7b show a simplified version of patterned rolls 104, 106. It is to be noted that the patterned rolls 104, 106 can have intermeshing male-female teeth defining any type of protrusion pattern.

Moreover, FIGS. 7a and 7b also show the web of starting material 100 as a simplified single-layer structure. In reality, the web of starting material 100 can also have a multi-layer structure including at least one or more of the layers (described above) which form sanitary napkin 20. Preferably, the web of starting material 100 has a multi-layer structure including the fluid-permeable cover layer 56 and one or more layers of the absorbent system 60. For example, the web of starting material 100 can include the fluid-permeable cover layer 56 and the transfer layer 62, both of which are simultaneously treated to form profiled component 108 that forms the upper treated component 75 that is later combined with the remaining components of the sanitary napkin 20. The web of starting material 100 includes material that has the ability to retain a shape imparted to it by the patterned rollers 104 and 106.

It should also be noted that although FIGS. 7a and 7b show a continuous method, other methods which are intermittent or discontinuous in nature remain within the scope of the present invention.

The absorbent articles of the present invention are advantageous in that the projections are characterized by a height and width that creates a desirable visual perception of thickness in an article that is relatively thin. Although various embodiments have been illustrated, this was for the purpose of describing, but not limiting, the invention. Various modifications will become apparent to those skilled in the art and are within the scope of this invention, which is defined more particularly by the attached claims.

The invention claimed is:

1. A sanitary absorbent article intended to be worn against a pudendal region of a user, said sanitary absorbent article having a thickness equal to or less than 5 mm, including a longitudinal centerline, and comprising:
a body contacting surface having a planar surface and a plurality of protrusions extending upwardly relative to said planar surface, wherein each of said protrusions has a height H and a width W; wherein H is at least about 0.5 mm and a ratio of the width W to the height H is in a range from about 2 to about 10; and
wherein a first protrusion and a second protrusion of said plurality of protrusions each include portions that are structured and arranged to intersect each other and each of said first and second protrusions including at least a portion that is separated from the other one of said first and second protrusion by said planar surface, each of said first and second protrusions extending across said longitudinal centerline and running obliquely with respect to said longitudinal centerline.

2. A sanitary absorbent article as defined in claim 1, wherein each of said protrusions is formed from at least one layer of said sanitary absorbent article.

3. A sanitary absorbent article as defined in claim 2, wherein each of said protrusions defines a simply connected space.

4. A sanitary absorbent article as defined in claim 1, wherein said absorbent article includes:
a fluid pervious cover layer;
a liquid-impervious barrier layer; and
an absorbent system located between said fluid-pervious cover layer and said liquid -impervious barrier layer, said absorbent system including a transfer layer and an absorbent core layer.

5. A sanitary absorbent article as defined in claim 4, wherein portions of at least two layers of the sanitary absorbent article positioned adjacent one another extend upwardly from the planar surface to thereby form said plurality of protrusions.

6. A sanitary absorbent article as defined in claim 5, wherein said at least two layers include at least one layer selected from the set consisting of the fluid-pervious cover layer, the transfer layer and the absorbent core layer.

7. A sanitary absorbent article as defined in claim 5, wherein said at least two layers are immediately adjacent one another.

8. A sanitary absorbent article as defined in claim 5, wherein said at least two layers are selected from the set consisting of the fluid-pervious cover layer, the transfer layer, the absorbent core layer and the liquid-impervious barrier layer.

9. A sanitary absorbent article as defined in claim 5, comprising a recess delimited by an untreated lower component and an upper treated portion that includes a protrusion.

10. A sanitary absorbent article as defined in claim 9, wherein said untreated lower component is substantially planar.

11. A sanitary absorbent article as defined in claim 10, wherein said recess includes a filler material.

12. A sanitary absorbent article as defined in claim 11, wherein said filler material is selected from the set consisting of super absorbent polymer and odor control material.

13. A sanitary absorbent article as defined in claim 9, wherein said recess has an elongated shape and forms a channel.

14. A sanitary absorbent article as defined in claim 5, wherein said protrusions extend towards a longitudinal centerline of said main body.

15. A sanitary absorbent article as defined in claim 5, wherein said protrusions define a protrusions pattern that is symmetrical about at least one of an imaginary longitudinal centerline and an imaginary transverse centerline.

16. A sanitary absorbent article as defined in claim 5, wherein at least one of said protrusions has an elongated shape.

17. A sanitary absorbent article as defined in claim 16, wherein the at least one of said protrusions extends along at least one of said imaginary longitudinal centerline and said imaginary transverse centerline.

18. A sanitary absorbent article as defined in claim 16, comprising two protrusions that share a common boundary.

19. A sanitary absorbent article as defined in claim 1, wherein said protrusions have a height H of at least 0.7 mm.

20. A sanitary absorbent article as defined in claim 1, wherein said protrusions have a height H of at least 1.0 mm.

21. A sanitary absorbent article as defined in claim 1, wherein said protrusions have a height H of at least 1.5 mm.

22. A sanitary absorbent article as defined in claim 1, wherein said protrusions have a ratio W/H ranging from about 4 to about 8.

23. A sanitary absorbent article as defined in claim 1, wherein said protrusions have a ratio W/H ranging from about 5 to about 7.

24. A sanitary absorbent article as defined in claim 9, wherein said sanitary absorbent article has a thickness T and said treated component has a thickness U, the ratio U/T being of at least 0.2.

25. A sanitary absorbent article as defined in claim 9, wherein said sanitary absorbent article has a thickness T and said treated component has a thickness U, the ratio U/T being of at least 0.6.

26. A sanitary absorbent article as defined in claim 1, comprising:
a first component including at least two superposed layers of material, said first component including the body contacting surface and a second main surface opposite said body contacting surface;
said first component including a recess on said second main surface registering with said protrusion, said recess having a boundary;
a second component including at least one layer of material, said second component being under said first component;
said first and second components defining a spacing therebetween, wherein the spacing within the boundary of said recess is greater than the spacing outside the boundary of said recess.

* * * * *